United States Patent [19]

Lindauer et al.

[11] Patent Number: 5,209,925
[45] Date of Patent: May 11, 1993

[54] STICK SHAVE FORMULATION AND ARTICLE EMPLOYING SAME

[75] Inventors: Jerome L. Lindauer, Hillsdale; Elizabeth M. Banko, South Amboy, both of N.J.

[73] Assignee: International Flavors & Fragrances Inc., New York, N.Y.

[21] Appl. No.: 929,831

[22] Filed: Aug. 14, 1992

Related U.S. Application Data

[62] Division of Ser. No. 805,020, Dec. 11, 1991, Pat. No. 5,174,992.

[51] Int. Cl.$^5$ ............................................. A61K 7/15
[52] U.S. Cl. ........................................ 424/73; 424/70; 424/DIG. 5; 252/351; 514/63; 514/558
[58] Field of Search .......................... 424/73, DIG. 5

[56] References Cited

U.S. PATENT DOCUMENTS

| | | | |
|---|---|---|---|
| 2,143,060 | 1/1939 | Dzialoschinsky | 424/73 |
| 2,838,442 | 6/1958 | McMaster | 424/73 |
| 2,876,161 | 3/1959 | Gieschi | 424/73 |
| 4,761,279 | 8/1988 | Khalil | 424/73 |
| 4,844,890 | 7/1989 | Suskin | 424/73 |
| 4,954,337 | 9/1990 | Gripp | 424/73 |
| 4,963,352 | 10/1990 | Roberts | 424/73 |
| 4,994,265 | 2/1991 | White | 424/73 |
| 5,034,220 | 7/1991 | Helioff | 424/73 |

FOREIGN PATENT DOCUMENTS 034522 2/1987 Japan .
004885 1/1992 Japan .

Primary Examiner—Thurman K. Page
Assistant Examiner—Raj Bawa
Attorney, Agent, or Firm—Arthur L. Liberman

[57] ABSTRACT

Described is a stick shave formulation and article employing said formulation. The stick shave formulation contains a triethanolamine stearate soap formed in situ with from 1-10% of a nonionic wetting agent; from 1-15% of a silicone copolymer; from 0.1-1% of a polyoxyethylene polymer slip agent; from 1-30% of a synthetic detergent; from 2-10% of a whitening agent; and 5-20% of emollient moisturizers and hair lubricants.

4 Claims, 1 Drawing Sheet

U.S. Patent May 11, 1993 5,209,925
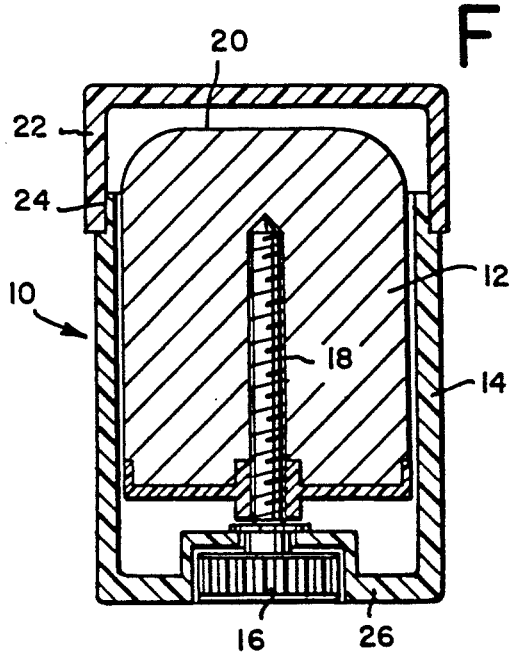
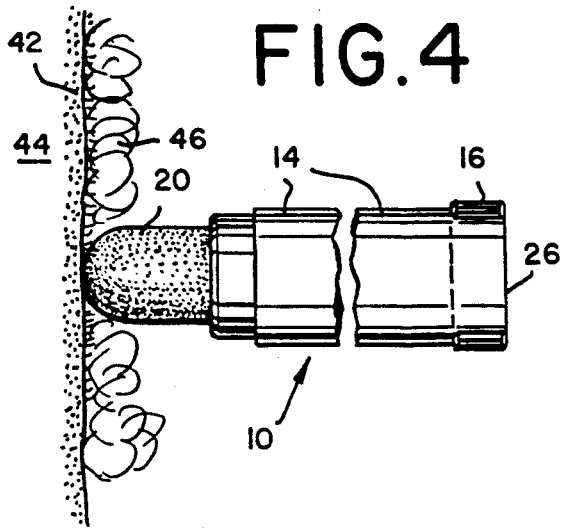
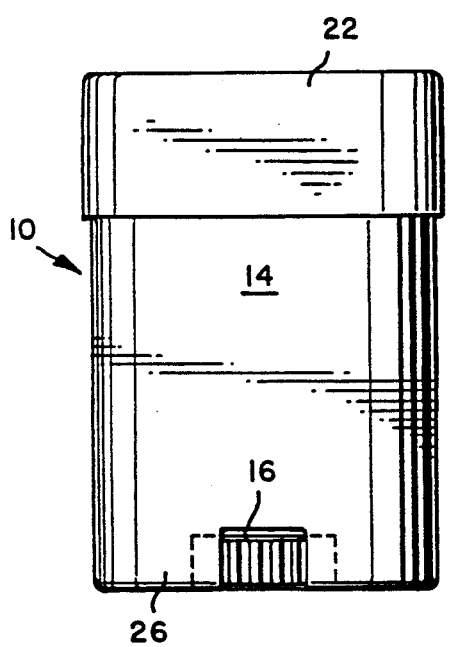
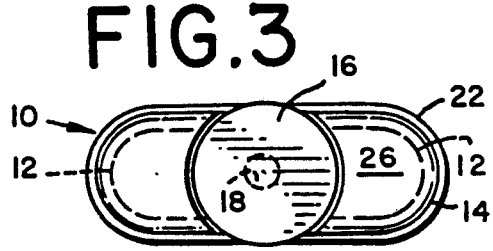
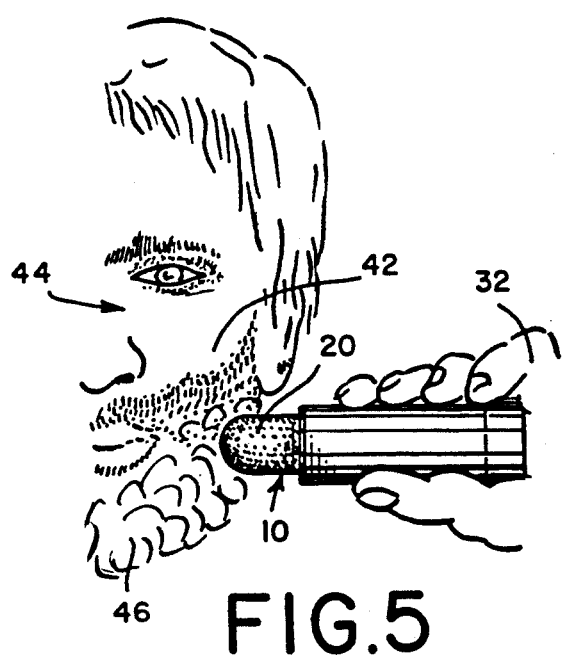

STICK SHAVE FORMULATION AND ARTICLE EMPLOYING SAME

This is a divisional of application Ser. No. 805,020, filed Dec. 11, 1991, now U.S. Pat. No. 5,174,992.

BACKGROUND OF THE INVENTION

Our invention describes a stick shave formulation and article for employing same. Traditional products used to facilitate wetting and lubricating the beard or in the case of women underarm or leg hair prior to shaving are generally soap systems that are packaged in pressurized aerosol containers or tubes. These products are inconvenient to use because the user must apply the products first to a hand and then to the face. The hand must then be washed prior to actually shaving Also pressurized systems contain volatile organic compounds as propellants and therefore are considered to be harmful to the environment. In addition products in commerce do very little in terms of lubricating, moisturizing or wetting.

Stick formulations using anti-perspirants and deodorants are known in the prior art; for example, the formula as described in U.S. Pat. No. 4,822,603 for "SURE ®" anti-perspirant and deodorant. Hair removers in the form of hand held "stick" articles are also known in the prior art and in commercial use, for example, the "NAIR ®" glide-on hair remover with aloe vera distributed by the Carter Products Division of Carter-Wallace, Inc., New York, New York 10153.

However, nothing in the prior art discloses either implicitly or explicitly the stick shave formulation and article for employing same of our invention.

SUMMARY OF THE INVENTION

Our invention relates to a convenient and easy to use shave system in stick form. The stick facilitates application of the product to the skin without the product actually touching the hands. The product contains superior wetting, lubricating and moisturzing ingredients.

The formulation of our invention contains a triethanolamine stearate soap formed in situ with from 1–10% of a nonionic wetting agent; from 1–15% of a silicone copolymer; from 0.1–1% of a polyoxyethylene polymer slip agent; from 1–30% of a synthetic detergent; from 2–10% of a whitening agent; and 5–20% of emollient moisturizers and hair lubricants.

The triethanolamine stearate soap formed in situ is formed because stearic acid and triethanolamine are in the formulation or group of formulations which are reacted in forming the formulation for the stick material. The nonionic wetting agent may be, for example, polyethylene glycol-50-nonylphenylether (e.g., IGEPON ®DM970 manufactured by the GAF Corporation of New York, New York). The silicone copolymer may be, for example, one of the copolymers having the structures:

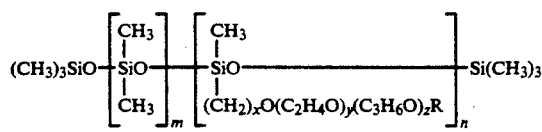

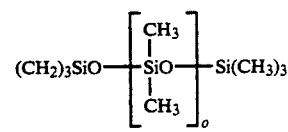

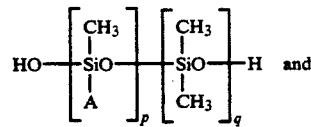

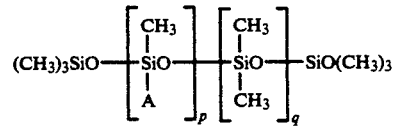

wherein
In the formulae (R = H or $_{1-3}$C alkyl;
m + n = 5–50;
x = 0–3;
y:z = (4:1) or (1:0);
the cpd. (I) contains 30–70 wt. % of polyoxyalkylene gps.;
A = $CH_2CH_2CH_2NH_2$ or $—CH_2CH_2CH_2NH—CH_2CH_2NH_2$;
O = 500–10,000;
p + q = 50–150).

The polyoxyethylene polymer slip agent may be a polyethylene glycol such as PEG 14-M or POLYOX WSRN 3000 (in 3% aqueous solution) manufactured by the Amerchol Corporation. The synthetic detergent may be, for example, sodium methyl cocoyl taurate (e.g., IGEPON ®TC42 manufactured by the GAF Corporation of New York, New York).

The whitening agent may be titanium dioxide, for example. The emollient moisturizers may be polyethylene glycol 600,000 (e.g., PEG 14-M, glyceryl mono stearate (e.g., CERASYNT Q, or AMERCHOL CAB (mixture of petrolatum and lanolin alcohol). The hair lubricant may be, for example, dimethicone polyol, which is DOW 193 surfactant manufactured by the Dow Chemical Company of Midland, Mich. In addition, fragrance, paraffin wax, methylparaben, propylparaben and the like may also be added to our formulation for enhancing its activity.

The inclusion of the polymer slip agent has given rise to unexpected, unobvious and advantageous results because such polymer slip agent actually lowers the friction between the razor and skin while at the same time not causing the solidified stick shave formulation to change phase at ambient conditions.

Formulations exemplary of our invention are set forth in Examples I and II, infra.

BRIEF DESCRIPTION OF THE DRAWINGS

FIG. 1 is a cut-away side elevation view of an article using the stick shave formulation of our invention.

FIG. 2 is a side view of an article of our invention using the stick shave formulation of our invention showing the internal parts of the article using "hidden" lines.

FIG. 3 is a bottom view of the article of FIGS. 1 and 2.

FIG. 4 shows the use of the article of FIGS. 1, 2 and 3 in operation when lathering skin.

FIG. 5 is another schematic diagram showing an individual using the article of FIGS. 1, 2 and 3.

DETAILED DESCRIPTION OF THE DRAWINGS

Referring to FIG. 1, a solid shaving stick 12 containing the formulation as exemplified in Examples I and II, infra, and as set forth, supra, is contained in a base holder 14 having a protective cap 22. When the user twists twister 16, screw 18 forces the gel stick 12 in an outward direction so that surface 20 can be easily used for lathering skin 42 on face 44 shown in FIG. 4. In FIG. 4 the lather is shown using reference numeral 46. The base of the holder 14 wherein the twister is contained is shown by reference numeral 26 in FIG. 2. The bottom of the article of FIG. 1 is shown in detail in FIG. 3 with the screw control shown by reference numeral 18 (using dotted lines) in FIG. 3.

Thus, an individual holds the article 10 of FIG. 1 in his or her arm 32 and lathers the skin 42 on face 44 (shown in FIGS. 4 and 5) with the lather being shown by reference numeral 46.

EXAMPLE I

The following groups of mixtures are prepared:

| Ingredients | Parts by Weight |
|---|---|
| Group A | |
| Stearic acid | 15.0 |
| Paraffin Wax | 10.0 |
| Glyceryl Stearate SE | 9.0 |
| Sodium Methyl Cocoyl Taurate | 6.0 |
| 50:50 Mixture of Petrolatum and Lanolin Alcohol | 4.0 |
| Nonyl Nonoxynol-150 | 3.0 |
| Propylparaben | 0.2 |
| Group B | |
| Titanium Dioxide | 8.0 |
| Group C | |
| Dimethicone Copolyol | 10.1 |
| Polyethylene Glycol 14-M | 8.0 |
| Triethanolamine | 1.5 |
| Methylparaben | 0.2 |
| Group D | |
| Sodium Cocoyl isethionate | 24.0 |
| Group E | |
| Fragrance | 1.0 |

All materials in Group A are weighed together and heated until melted.

The materials in Group B are added to the materials in Group A and the resulting mixture is mixed until uniform.

All materials and parts are weighed together and heated until completely melted. The materials of Part D are added to Part C and mixed until uniform.

The mixture resulting from Parts A and B are added to the mixture resulting from Parts C and D until a smooth consistency is formed. To the resulting mixture, the fragrance of Part E is added with mixing.

The resulting product while still hot is then added into molds and the molds are allowed to cool and harden. Each mold is then fabricated into an article as set forth in FIGS. 1, 2 and 3.

A shaving stick thus formulated when used with water imparts a white emollient foam for shaving ease.

EXAMPLE II

Shaving Stick

The following mixtures are prepared:

| Ingredients | Parts by Weight |
|---|---|
| GROUP "A" | |
| Stearic Acid | 15.00 |
| Parraffin Wax 155/160 | 10.00 |
| CERASYNT (VAN DYKE) (NOTE: 1) | 9.00 |
| Igepon TC42 (GAF) (NOTE: 2) | 6.00 |
| Amerchol CAB (AMERCHOL) (NOTE: 3) | 4.00 |
| IGEPON DM970 (GAF) (NOTE: 4) | 3.00 |
| PROPYL PARABEN | 0.20 |
| GROUP "B" | |
| TITANIUM DIOXIDE #328 (WHITTAKER) | 8.00 |
| GROUP "C" | |
| DOW 193 SURFACTANT (DOW CORNING) (NOTE: 5) | 10.10 |
| POLYOX WSRN 3000 IN 3% SOLUTION (AMERCHOL) (NOTE: 6) | 8.00 |
| TRIETHANOLAMINE 99% | 1.50 |
| METHYL PARABEN | 0.20 |
| GROUP "D" | |
| IGEPON AC78 (GAF) (NOTE: 7) | 24.00 |
| GROUP "E" | |
| FRAGRANCE IFF | 1.00 |

NOTE 1: CERASYNT Q is glyceryl monostearate.
NOTE 2: IGEPON TC42 is sodium methyl cocoyl taurate.
NOTE 3: AMERCHOL CAB is a mixture of petrolatum and lanolin alcohol.
NOTE 4: IGEPON DM970 is polyethylene glycol-50-nonyl phenylether.
NOTE 5: DOW 193 SURFACTANT is dimethicone copolyol (a silicone copolymer).
NOTE 6: POLYOX WSRN 3000 is a 3% aqueous solution of polyoxyethylene-14,000 (molecular weight).
NOTE 7: IGEPON AC78 is sodium cocoyl isethionate.

All the materials in Group "A" are mixed together and heated until a melt is formed.

The material of Group "B" (TITANIUM DIOXIDE) is added to the mixture of Group "A" and the resulting mixture is stirred until uniform.

All the materials in Group "C" are weighed and mixed together and heated until a melt is formed. The resulting melt is admixed with the material of Group "D" (IGEPON AC78) until the resulting mix is uniform.

The mixture of Groups "A" and "B" is admixed with the mixture of Groups "C" and "D" until a new mixture is formed having smooth consistency. The resulting mixture is admixed with the Fragrance of Part "E".

While hot the resulting mixture is poured into molds and the resulting articles are allowed to cool and harden thereby forming a shaving stick which when used with water imparts a white emollient foam for shaving ease.

What is claimed is:

1. A solid phase shaving stick formulation for use in forming a solid phase shaving stick article, said article being in the solid phase prior to, during and subsequent to use thereof, consisting essentially of:
    (i) from about 1 up to about 10% by weight of a nonionic wetting agent which is a polyethylene glycol nonyl phenyl ether;
    (ii) from about 1 up to about 15% by weight of a silicone copolymer;
    (iii) from about 0.1 up to about 1% by weight of a polyoxyethylene polymer slip agent;
    (iv) from about 1 up to about 30% of a synthetic detergent selected from the group consisting of sodium methyl cocoyl taurate and sodium cocoyl isethionate;
    (v) from about 2 up to about 10% by weight of a titanium dioxide whitening agent; and
    (vi) from about 5 up to about 20% by weight of an emollient moisturizer selected from the group consisting of:

(a) a polyethylene glycol;
(b) glyceryl monostearate; and
(c) a mixture of petrolatum and lanolin alcohol with the remainder being a mixture of stearic acid and triethanolamine.

2. The composition of claim 1 wherein the weight ratio of stearic acid:triethanolamine is about 10:1.

3. A shaving stick article comprising the formulation of claim 1.

4. A shaving stick article comprising the formulation of claim 2.

* * * * *